US006677477B2

(12) United States Patent
Pohjanvesi et al.

(10) Patent No.: US 6,677,477 B2
(45) Date of Patent: Jan. 13, 2004

(54) PROCESS FOR THE PRODUCTION OF PERACETIC ACID

(75) Inventors: Seppo Pohjanvesi, Oulu (FI); Arto Pukkinen, Kempele (FI); Teemu Sodervall, Oulu (FI)

(73) Assignee: Kemira Chemicals Oy, Helsinki (FI)

( * ) Notice: Subject to any disclaimer, the term of this patent is extended or adjusted under 35 U.S.C. 154(b) by 0 days.

(21) Appl. No.: 10/114,178

(22) Filed: Apr. 3, 2002

(65) Prior Publication Data
US 2002/0193626 A1 Dec. 19, 2002

(30) Foreign Application Priority Data
Apr. 4, 2001 (FI) .............................. 20010705

(51) Int. Cl.$^7$ ............................. C07F 409/26
(52) U.S. Cl. ............................. 562/6; 562/4
(58) Field of Search .................. 562/2, 3, 4, 6

(56) References Cited

U.S. PATENT DOCUMENTS

| 2,347,434 | A | | 4/1944 | Reichert et al. | |
| 3,168,554 | A | * | 2/1965 | Phillips et al. ............... | 562/3 |
| 3,264,346 | A | | 8/1966 | Weiberg | |
| 4,051,059 | A | * | 9/1977 | Bowing et al. ........ | 252/186.23 |
| 4,088,676 | A | * | 5/1978 | Hofen et al. .................... | 562/6 |
| 4,115,410 | A | | 9/1978 | Watts | |
| 4,278,615 | A | * | 7/1981 | Stober et al. ................... | 562/6 |
| 4,297,298 | A | * | 10/1981 | Crommelynck et al. ....... | 562/3 |
| 5,030,381 | A | * | 7/1991 | Zimmermann et al. | 252/186.26 |
| 5,098,607 | A | * | 3/1992 | Inaba et al. ................. | 252/384 |
| 5,656,302 | A | * | 8/1997 | Cosentino et al. .......... | 424/616 |
| 5,886,216 | A | * | 3/1999 | Pudas ............................ | 562/6 |

FOREIGN PATENT DOCUMENTS

| EP | 0 296 328 | 12/1988 |
| EP | 0 798 016 B1 | 8/1997 |
| EP | 0937754 | 8/1999 |
| EP | 1 004 576 A1 | 5/2000 |
| GB | 1014361 | 3/1963 |
| GB | 949094 | 2/1964 |
| WO | 9932710 | 7/1999 |
| WO | 9943756 | 9/1999 |
| WO | 0052258 | 9/2000 |

* cited by examiner

*Primary Examiner*—Jean F. Vollano
(74) *Attorney, Agent, or Firm*—Young & Thompson

(57) ABSTRACT

The reaction medium and distillate of a conventional continuous peracetic acid process can be combined into a stable peracetic acid product if the acid catalyst present in the reaction medium is neutralized.

27 Claims, 1 Drawing Sheet

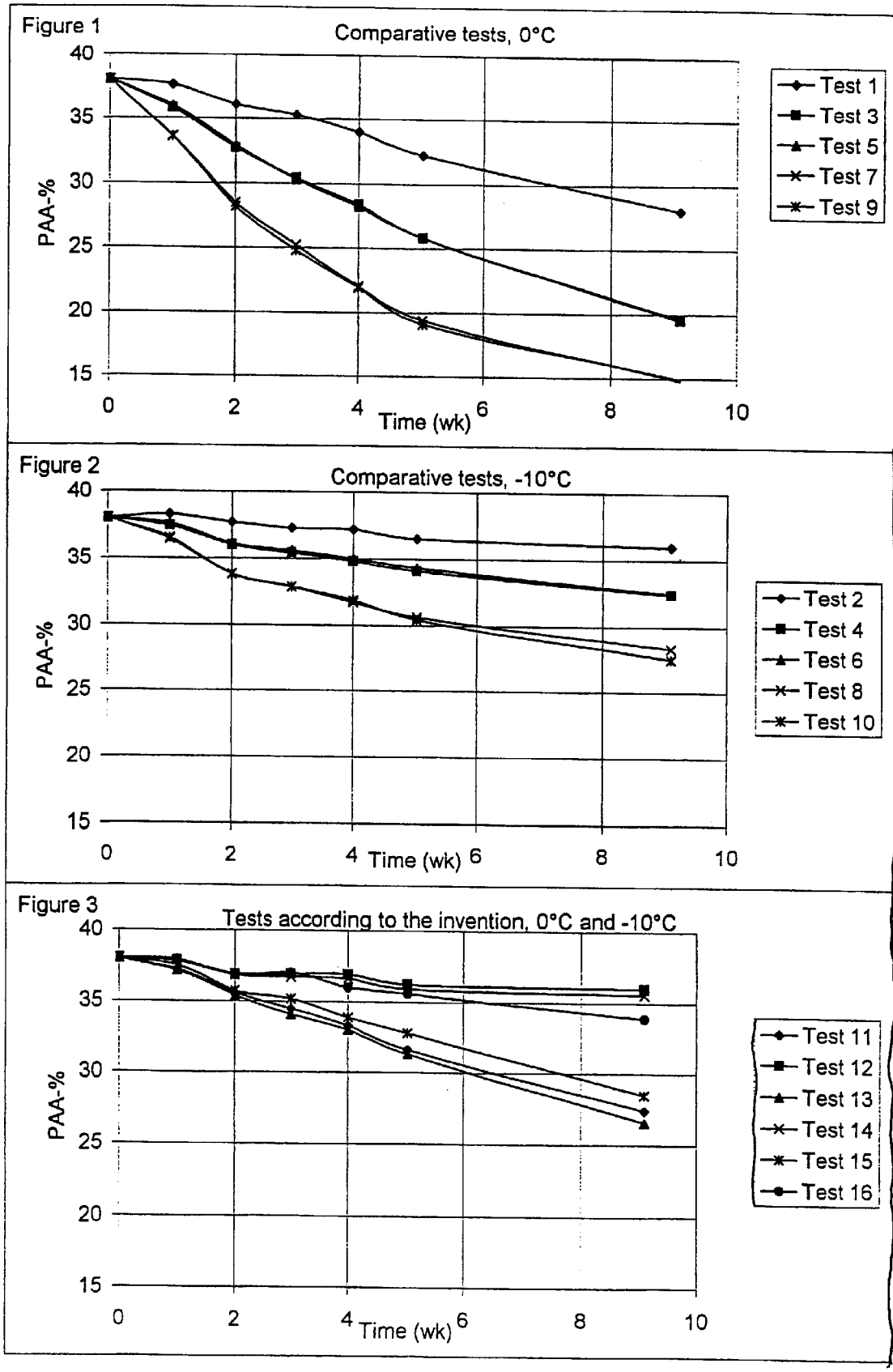

PROCESS FOR THE PRODUCTION OF PERACETIC ACID

BACKGROUND OF THE INVENTION

The invention relates to a process for the production of a stable peracetic acid product by feeding hydrogen peroxide and acetic acid continuously into an aqueous reaction medium that contains hydrogen peroxide, acetic acid, peracetic acid and an acid catalyst, in which medium the hydrogen peroxide and acetic acid react and form peracetic acid, and by distilling a peracetic acid concentrated distillate continuously from the reaction medium. The invention also relates to a stabilized peracetic acid product and a process for the stabilization of a product containing peracetic acid, water and other substances.

DESCRIPTION OF THE RELATED ART

Peracetic acid can be used as both a bleaching chemical and a disinfection chemical. Distilled peracetic acid (dPAA), being an environment-friendly chemical, is very well suited for the bleaching of pulp. With the help of peracetic acid, the total selectivity of TCF bleaching (Total Chlorine Free) can be improved by the use of acid delignification steps between alkaline steps (Kemira patent application No. FI 974575). Besides delignification, the peracetic acid step also improves pulp brightness, for which reason it is excellently suited for the after-bleaching of both ECF and TCF pulps (Kemira patent application No. FI 990445).

The disinfectant properties of peracetic acid are exploited, for example, in the improving of the shelf life of pigment suspensions, which enables waste paste to be recycled (FI patent application 982735) in paper mills. The bleaching properties of peracetic acid can also be exploited in the bleaching of the pigment suspension used in the paper machines (FI 980417).

In the storage and transport of distilled peracetic acid, the special characteristics of the chemical must be taken into account. In order to inhibit the decomposition ($H_2O_2 \rightarrow H_2O + \frac{1}{2}O_2$) characteristic of peroxides, the product is stabilized in connection with its production. Regarding peracetic acid it is also to be taken into account that both its storage and its transport must take place under refrigeration. At an elevated temperature, distilled peracetic acid reverts to its initial substances, whereby a so-called equilibrium mixture of peracetic acid is formed ($CH_3COOOH + H_2O \rightarrow CH_3COOH + H_2O_2$).

In cellulose mills and in the bleaching of pigments, large amounts of peracetic acid are required regardless of whether the question is of production or of full-scale trial runs. Through on-site production, storage and transport are avoided.

In connection with continuous-working production of distilled peracetic acid there always forms, as a byproduct, the medium of the peracetic acid process, the so-called bottom product ($ePAA_b$), i.e. an equilibrium mixture; an effort is made to maintain its composition in a stationary state. During the process, small amounts of impurities also concentrate in the reaction medium, and thus this rather dilute peracetic acid solution, i.e. the bottom product of distillation ($ePAA_b$), contains, among other things, all of the metallic impurities originating in the raw materials, primarily in acetic acid. Its storage and transport must therefore be carried out with great care.

It is generally known to prepare peracetic acid by feeding hydrogen peroxide and acetic acid continuously into an aqueous reaction medium which contains hydrogen peroxide, acetic acid, peracetic acid and an acid catalyst and in which hydrogen peroxide and acetic acid react and form peracetic acid, and by distillating a peracetic acid concentrated distillate continuously from the reaction medium (Degussa U.S. Pat. No. 3,264,346, DGS GB 949,094, FMG GB 1,014,361, Degussa EP 296 328, Eka Chemicals EP 789 016, Solvay EP 1 004 576). Both distilled peracetic acid and the said reaction medium are obtained as products.

In known processes, the bottom product, i.e. the spent reaction medium (ePAA) is mentioned only as a problematic byproduct (as an effluent).

SUMMARY OF THE INVENTION

The object of the present invention is to provide a process for the exploitation of the spent reaction medium. When a reaction medium $ePAA_b$ containing hydrogen peroxide, acetic acid, a small amount of peracetic acid and an acid catalyst is mixed as such with a peracetic acid concentrated distillate dPAA, the $ePAA_b$+dPAA stability of the forming mixture is very poor, and its peracetic acid concentration decreases rapidly during storage. It has also been observed, unexpectedly, that even cold storage (0° C.–10° C.) is not alone capable of stabilizing the peracetic acid product.

The problem has now been solved by a new process for the production of a stable peracetic acid product, the process being mainly characterized in the bringing together of the distillate, the reaction medium and a substance that at least partly neutralizes the acid catalyst.

The inventive idea of the present invention is thus that the bottom product formed as a byproduct, i.e. the spent reaction medium of the distillation of peracetic acid, can be combined with the actual product. The acid catalyst arriving along with the bottom product is neutralized before the mixing. Thus the storage and transport of a dilute and less pure peracetic acid is avoided.

BRIEF DESCRIPTION OF THE DRAWING

FIGS. 1–2 show comparative test results.

FIG. 3 shows test results for the invention.

DESCRIPTION OF THE PREFERRED EMBODIMENT

According to one embodiment of the invention, the removal of the reaction medium and its combining with the distillate and the neutralizing agent is also carried out continuously. In this case the reaction medium is removed in an amount which is at the desired ratio to the forming distillate and is combined with the distillate and the neutralizing agent.

According to another embodiment, the reaction medium is removed batchwise, for example when the impurity level has risen so high that the production of peracetic acid is disturbed. The recovered reaction medium that contains impurities, i.e. in this case the bottom product, is thereafter combined with the distillate and a neutralizing agent. It has also been observed unexpectedly that metallic impurities do not reduce the stability of the peracetic acid product.

In the invention, the reaction medium and the distillate can be combined at any ratio. This means that the agent neutralizing the acid catalyst stabilizes the mixture of the reaction medium and the distillate regardless of the ratio of these components.

In terms of the usability of the product it is, however, typical that the weight ratio of the distillate to the reaction medium is within the range 1:50–500:1, preferably within the range 1:1–100:1, even more preferably within the range 4:1–40:1, and most preferably within the range 10:1–30:1.

Likewise, it is preferable to mix together the distillate, the reaction medium and the neutralizing agent so that the peracetic acid concentration in the forming mixture will be 10–68% by weight, preferably 29–59% by weight.

The acid catalyst is a typical acid accelerating the equilibrium reactions (hydrogen peroxide+acetic acid⇌peracetic acid+water). Preferably it is an inorganic acid or a mixture thereof, the inorganic acid being even more preferably phosphoric acid or sulfuric acid, and most preferably sulfuric acid.

The acid catalyst concentration is such that a maximal peracetic acid production is obtained. When hydrogen peroxide and acetic acid are added to the reaction mixture and peracetic acid and water are removed from it, the acid catalyst must be capable of accelerating the reaction to the right in the above equilibrium reaction in accordance with the technical requirements. The concentration of the acid catalyst can be expressed so that it corresponds to the concentration of the most common catalyst, i.e. sulfuric acid. A preferable concentration of sulfuric acid in the reaction medium is within the range 1–20% by weight, a more preferable one within the range 1–10% by weight, and the most preferable within the range 1–4% by weight.

By at least partial neutralization of the acid catalyst is meant that the lowering effect of the acid catalyst on the pH of the reaction mixture is reduced or eliminated. When the effect is eliminated, the product continues to be acid, since it contains peracetic acid and a small amount of acetic acid. The neutralizing agent must be capable to neutralizing the acid catalyst without having a negative effect on the useful properties of the product. Preferably it is an inorganic base, a substance forming an inorganic base, or a mixture containing either of the two, the inorganic base being more preferably an alkali metal hydroxide or an alkaline earth metal hydroxide, most preferably sodium hydroxide. When the neutralizing agent is sodium hydroxide, it is preferably mixed together with the distillate and the reaction medium as an aqueous solution having a concentration of 20–60% by weight, preferably 40–50% by weight.

Preferably the acid catalyst is neutralized completely, in which case the neutralizing agent is contacted with the distillate and the reaction medium in a substantially stoichiometric amount relative to the acid catalyst amount. This means, for example, that there is added to the reaction mixture two moles of sodium hydroxide (80 g) per each mole of sulfuric acid (98 g) in the mixture.

Even though the reaction medium, the distillate and the neutralizing agent can be brought together in any order, it is especially preferable to proceed so that first the reaction medium and the neutralizing agent are mixed together to form a mixture in which the acid catalyst is at least partly neutralized, and thereafter this mixture is mixed together with the distillate. In the process according to the invention the above-mentioned three principal components can also be mixed together with other components.

If what is in question is the reaction medium of the continuous-working peracetic acid process described above, its pH before the mixing is typically within the range 0.001–1.0, even more typically within the range 0.01–0.5 and most typically within the range 0.02–0.2.

A typical reaction medium used in the present invention contains the following ingredients and amounts of ingredients. The hydrogen peroxide concentration is typically within the range 4–40% by weight, preferably within the range 5–30 by weight, and most preferably within the range 10–20% by weight. The acetic acid concentration is typically within the range 0.1%–40% by weight, preferably within the range 1–30% by weight, most preferably within the range 15–30% by weight. The molar ratio of hydrogen peroxide to acetic acid is typically within the range 0.3:1–30:1, preferably within the range 0.5:1–10:1. The peracetic acid concentration is typically within the range 1–30% by weight, preferably within the range 5–20% by weight.

The acid catalyst concentration in the reaction medium is typically such that its catalytic effect corresponds to a sulfuric acid concentration that is within the range 0.3–30% by weight, preferably within the range 1–20% by weight, most preferably within the range 1–10% by weight. The water concentration is typically within the range 10–75% by weight, preferably within the range 20–60% by weight, most preferably within the range 30–50% by weight. The reaction medium typically contains a stabilizer that has preferably been selected from among phosphonic acids, their salts and dipicolinic acid sodium salt, or any mixture of these. Typical stabilizers are cited on lines 45–58 of the right-side column of page 2 of publication EP-B 1-0 789 016. A preferable stabilizer concentration in the reaction medium is within the range 0.05–1% by weight, most preferably within the range 0.1–0.4% by weight. It is preferable to use 1-hydrocyethylene-1,1-diphosphonic acid and/or sodium salt of dipicolinic acid.

In the process according to the invention it is preferable to maintain the stationary state of the reaction medium by feeding into it as many moles of hydrogen peroxide and acetic acid as peracetic moles are removed from it and by maintaining the reaction medium at a temperature of 40–60° C., in which case the velocities of the equilibrium reaction will be sufficiently high.

In the process according to the invention, there is in principle no acid catalyst in the distillate. Thus the hydrogen ion concentration in the distillate, i.e. its pH value, is derived from the peracetic acid present in it. The acetic acid concentration of the distillate is in general low, and its effect is not taken into account in this context. Typically the pH of the distillate before the mixing together of the distillate, the reaction medium and the neutralizing agent is within the range 1–3, preferably within the range 1.5–2.5. The distillate contains little hydrogen peroxide, and thus its hydrogen peroxide concentration is typically below approximately 1% by weight, preferably within the range 0.1–0.5% by weight. Respectively, the acetic acid concentration in the distillate is below approximately 1% by weight, preferably within the range 0.05–0.5% by weight.

The peracetic acid concentration in the distillate depends on the distillation conditions. Typically the distillate is produced by distilling the reaction medium at a temperature of 40–60° C. and at a reduced pressure of 30–120 mbar. In general the distillation conditions arranged are such that the peracetic acid concentration in the distillate obtained is within the range 10–70% by weight, preferably within the range 30–60% by weight. Respectively the water content in the distillate is within the range 20–80% by weight, preferably within the range 40–70% by weight. It is possible to add to the distillate a stabilizer, which is preferably selected from among phosphonic acids, salts thereof, dipicolinic acid, salts thereof, or any mixture thereof. Typical stabilizers are cited, for example, on lines 45–58 of the right-side column of page 2 of the above-mentioned publication EP-B1-0 789 016. The stabilizer concentration is typically within the range 0.001–0.5% by weight, preferably within the range 0.01–0.1% by weight. Most preferably, 1-hydroxyethylene-1,1-diphosphonic acid (Dequest 2010) and/or sodium salt of dipicolinic acid is used.

Of the three principal components to be mixed together, the reaction medium is the most acidic, since it contains an acid catalyst, which is in general a strong inorganic acid. If the reaction medium did not contain an acid catalyst, it would, owing to its lower peracetic acid and acetic acid concentrations, be less acidic than the distillate. In general, the distillate, the reaction medium and the neutralizing agent are mixed together so that the pH of the forming mixture is within the range 1.0–3.0, preferably within the range 1.0–2.0.

It is additionally advantageous, in connection with or after the mixing together of the distillate, the reaction medium and the agent at least partly neutralizing the acid catalyst, to cool the ingredients and/or the mixture preferably to a temperature within the range $-10-\pm 0°$ C. and to keep it preferably at that temperature. The stability of the product is thus affected both by the pH and by the temperature.

The invention which is the object of the application also relates to a stabilized peracetic acid product. The peracetic acid product is characterized in that it contains hydrogen peroxide, acetic acid, peracetic acid, water and a substantially neutral salt of an inorganic acid.

The substantially neutral salt of an inorganic acid is preferably the salt of a strong inorganic acid and a strong base. The peracetic acid product contains the substantially neutral salt of an inorganic acid preferably in an amount of 0.03–2.2% by weight, still more preferably 0.07–1.5% by weight, most preferably 0.07–0.75% by weight, calculated equimolarly as sodium sulfate.

The stability effect is not limited to any specific peracetic acid concentration. However, in practice the peracetic acid product contains peracetic acid approximately 10–68% by weight, preferably 29–59% by weight, the remainder being mainly made up of water and small proportions of hydrogen peroxide, acetic acid and possible impurities.

Finally the invention relates to the use of a base for the stabilization of an acid peracetic acid product that contains another acid, stronger than peracetic acid. It has namely been observed, unexpectedly, that the peracetic acid of the said acid product will not keep even if the product is stored at low temperatures of 0° C.–-10° C. Instead, a base improves the shelf life of the product considerably. The acid stronger than peracetic acid is preferably an inorganic acid or a mixture thereof, the inorganic acid being more preferably phosphoric or sulfuric acid, most preferably sulfuric acid. The concentration of sulfuric acid is preferably within the range 1–20% by weight, more preferably within the range 1–10% by weight, most preferably within the range 1–4% by weight. The base is preferably an inorganic base, a substance forming it, or a mixture containing either one of them, the inorganic base being preferably an alkali or alkaline earth metal hydroxide and most preferably sodium hydroxide. Preferably the amount of the base contacted with the peracetic acid product is substantially stoichiometric relative to the amount of the acid stronger than peracetic acid.

The peracetic acid product will stabilize substantially regardless of its peracetic acid concentration. In practice the product is derived from the peracetic acid process, in which case it contains peracetic acid within the range 10–68% by weight. In this case the pH is adjusted to a value approximately within the range 1.0–3.0. Preferably the product contains peracetic acid approximately 29–59% by weight, in which case the pH is adjusted to a value approximately within the range 1.0–2.0.

In principle the product to be neutralized may contain any ingredient that gives it a pH value other than that required by the peracetic acid amount present in it. Since usually an acid catalyst is used in the process for producing peracetic acid, the product preferably contains an inorganic acid, in which case the pH of the product is adjusted to the said value by means of a base.

Typically the said base is in the form of an aqueous sodium hydroxide solution having a concentration of 20–60% by weight, preferably 40–50% by weight.

As stated above, the peracetic acid product is preferably taken from the peracetic acid process. Advantageously it is the product of the process described above, i.e. it is made up of the reaction medium and distillate of a peracetic acid process wherein hydrogen peroxide and acetic acid are fed continuously into a reaction medium that contains hydrogen peroxide, acetic acid, peracetic acid and a catalyst made up of the said inorganic acid, and a peracetic acid concentrated distillate is distilled continuously from the reaction medium.

Below, examples are presented the sole purpose of which is to elucidate the invention that is the object of the application.

EXAMPLES

In the examples, the peracetic acid stability of the forming mixture was investigated when there were mixed together the hydrogen peroxide of a typical peracetic acid process, acetic acid, peracetic acid, sulfuric acid, and an aqueous reaction medium ePAA$_b$, a distillate dPAA containing mainly peracetic acid and water, and a substance neutralizing sulfuric acid.

Test Arrangements

The following four variables were used in the tests:
1) The proportion of the bottom product (ePAA$_b$) of the distillation in the distillate (dPAA) was 0.2 and 5% of the total weight of the peracetic acid (100% PAA),
2) a pure ePAA$_b$ solution and an ePAA$_b$ solution contaminated with metal ions (5 ppm Fe$^{2+}$, 1.3 ppm Cr and some Ni) were used,
3) a neutralized ePAA$_b$ solution (performance) and an unneutralized solution (control) ePAA$_b$ were used,
4) storage temperatures of 0° C. and -10° C. were used.

The effect of these variables on a mixture made up of dPAA and ePAA$_b$ was investigated.

ePAA$_b$ product in amounts of 0.2 and 5% by weight were added to a dPAA solution. Two types of ePAA$_b$ were prepared: one pure and one contaminated to which there had been added a metal salt typically accumulating in the reaction medium of the production process. The neutralizing agent used was sodium hydroxide, which was added to the ePAA$_b$ product before the latter was mixed together with the dPAA solution.

The samples were stored at temperatures of 0 and -10° C. The analysis of the products was started immediately after their preparation and was terminated approximately 9 weeks later. Their concentrations of PAA (=peracetic acid), H$_2$O$_2$ (hydrogen peroxide) and AA (acetic acid) were measured within one day from their preparation and thereafter once a week until the end of the test period. The concentrations of sulfuric acid, Dequest 2010 stabilizer (=HEDPA=1-hydroxyethylene-1,1-diphosphonic acid) and dipicolinic acid (DPA=2,6 pyridene dicarboxylic acid) stabilizer were analyzed at the beginning of the test and at one month.

The dPAA solution was stabilized with 200 ppm of Dequest 2010 stabilizer and 50 ppm of DPA. In the ePAA$_b$ product the respective stabilizer amounts were slightly larger, i.e. 2000 ppm and 200 ppm. Thus the stabilizer amounts in the dPAA-ePAA$_b$ mixture increased somewhat when more ePAA$_b$ was used.

A 48% by weight sodium hydroxide was used for the neutralization of the sulfuric acid. It was used in such an amount that the added molar amount of sodium hydroxide was approximately the same as the sulfuric acid amount present in the ePAA$_b$, in which case the final pH obtained was within the range 1.3–1.5. When a small excess of sodium hydroxide was used, the final pH obtained was 2.

The variables of the examples and their values are shown in Table 1. In order to facilitate comparison, the initial PAA percentage was for all the mixtures from "normal" to 38%.

TABLE 1

Variables in the examples and the result of the test after 9 weeks

| Test | dPAA % | ePAA$_b$ % | Fe contamination, ppm | Neutralized H$_2$SO$_4$, pH | Storage temperature ° C. | Result at end of test PAA-% |
|---|---|---|---|---|---|---|
| 1 (control) | 100 | 0 |   |   | 0 | 28.0 |
| 2 | " | " | " |   | -10 | 36.0 |
| 3 | " | 98 | 2 |   | 0 | 19.5 |
| 4 | " | " | " |   | -10 | 32.4 |
| 5 | " | " | " | 5 | 0 | 19.6 |
| 6 | " | " | " | 5 | -10 | 32.5 |
| 7 | " | 95 | 5 |   | 0 | 14.8 |
| 8 | " | " | " |   | -10 | 28.3 |
| 9 | " | " | " | 5 | 0 | 14.9 |
| 10 | " | " | " | 5 | -10 | 27.5 |
| 11 (perf.) | " | " |   | 1.49 | 0 | 27.4 |
| 12 | " | " |   | " | -10 | 36.0 |
| 13 | " | " | 5 | 1.25 | 0 | 26.6 |
| 14 | " | " | " | " | -10 | 35.6 |
| 15 | " | " | " | 2.00 | 0 | 28.5 |
| 16 | " | " | " | " | -10 | 33.9 |

The stabilizer concentrations varied very little: Dequest 2010 within the range 200–300 ppm and DPA within the range 50–60 ppm, depending on the concentration of the ePAA$_b$ product in the mixture.

Results

The results are shown in the last column of Table 1 and graphically in FIGS. 1, 2 and 3.

FIG. 1 depicts the effect of the concentration of ePAA$_b$ on the decreasing of the PAA concentration in the mixture, as a function of time at 0° C.

FIG. 2 depicts the respective results at −10° C.

FIG. 3 depicts the effect of the ePAA$_b$ concentration on the decreasing of the PAA concentration in the mixture, as a function of time at temperatures of 0° C. and −10° C. when sulfuric acid neutralization according to the invention is used.

On the basis of Tests 1–16 it can be noted that

In the samples according to the invention, from which the acidity of the sulfuric acid had been eliminated, the concentration of PAA remained high Metallic impurities did not have a significant effect in these tests on the decreasing of the concentration of PAA It was also observed that the equilibrium reaction:

$$AA + H_2O_2 \rightleftharpoons PAA + H_2O$$

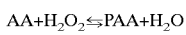

also occurs at storage temperatures of 0–−10° C. When the ratio ePAA$_b$/dPAA is high, the reverse reaction (to the left in the reaction equation) is rapid. If the sulfuric acid is neutralized, the mixture stabilizes, since the decreasing of PAA is in that case as slight as in the 0-sample devoid of sulfuric acid.

TABLE 2

Effect of sulfuric acid on the reverse reaction, i.e. decomposition, of PAA

| Proportion of ePAA$_b$ | H$_2$SO$_4$ | H$_2$SO$_4$ neutralized with | Storage temperature | |
|---|---|---|---|---|
| | | | 0° C. | −10° C. |
| | | | Decrease of PAA | |
| % | % | NaOH | % units/wk | % units/wk |
| 0 | 0 |   | 1.0 | 0.2 |
| 2 | 0.06 | No | 2.4 | 0.8 |
| 5 | 0.15 | No | 4.0 | 1.6 |
| 5 | 0.15 | Yes | 1.2 | 0.4 |

The neutralization of sulfuric acid was carried out with a sodium hydroxide solution. In one case the neutralization was carried out with a stoichiometric amount of sodium hydroxide relative to the sulfuric acid (2 moles of NaOH per one mole of H$_2$SO$_4$), in which case the final pH was 1.4. This pH corresponds to the pH value given by the remaining peracetic acid and acetic acid. In another case an excess (16%) of sodium hydroxide relative to the amount of sulfuric acid was added, in which case the final pH was 2.0. On the basis of the results, a stoichiometric amount of sodium hydroxide relative to the sulfuric acid sufficed to stabilize the mixture, whereas an excess of sodium hydroxide somewhat reduced the stability of the mixture. It was also observed that a good result presupposed the neutralizing of the acid catalyst in the ePAA$_b$ product with a neutralizing agent immediately before its being mixed with the dPAA solution. The pH values of the ePAA$_b$ solution and the sodium hydroxide amounts used in it are shown in Table 3.

TABLE 3

| ePAA$_b$ % | H$_2$SO$_4$ % | Initial pH | Neutralized H$_2$SO$_4$ 48% NaOH kg/t ePAA$_b$ | Final pH | Na % | Note |
|---|---|---|---|---|---|---|
| 13 | 3 | 0.03 | 0 | 0.1 | 0 | |
| | 3 | 0.08 | 51.0 | 1.4 | 1.41 | Stoichiom. |
| | 3 | 0.08 | 59.2 | 2.0 | 1.63 | NaOH excess |

SUMMARY

In the tests performed, there was mainly used a mixture containing 95% by weight of dPAA solution and 5% by weight of ePAA$_b$ product. The concentrations of the various components are shown in Table 4.

TABLE 4

| | PAA % | AA % | H$_2$O$_2$ % | H$_2$O % |
|---|---|---|---|---|
| DPAA | 45 | 0.1 | 0.3 | 54.6 |
| ePAA$_b$ | 13 | 22 | 15 | 44.5 |
| DPAA/ePAA$_b$ | 38 | 1 | 0.9 | 39.8 |

It was observed in the tests that ePAA$_b$ can be mixed with dPAA. If the sulfuric acid present in the ePAA$_b$ is not neutralized, the peracetic acid reverts to its raw materials. In the dPAA/ePAA$_b$ mixture, 4% and 1.4% of the PAA reverts in a week to acidic acid and hydrogen peroxide when the temperature is respectively 0° C. and −10° C. When sulfuric acid was neutralized the respective values were 1.2% and 0.4%. For dPAA alone the respective values were 1.0% and 0.2%. A summary of the results is presented in Table 5.

TABLE 5

| DPAA/ ePAA$_b$ %/% | H$_2$SO$_4$ % | H$_2$SO$_4$ neutralized with NAOH | Storage temperature 0° C. PAA decrease % units/wk | −10° C. PAA decrease % units/wk |
|---|---|---|---|---|
| 100/0 | 0 | — | 1.0 | 0.2 |
| 95/5 | 0.15 | No | 4.0 | 1.6 |
| 95/5 | 0.15 | Yes | 1.2 | 0.4 |

What is claimed is:

1. A continuous process for the stable production of a stable peracetic acid product, comprising the steps of:
continuously feeding hydrogen peroxide and acetic acid to a reaction medium comprising an acid catalyst to form peracetic acid within the reaction medium;
continuously distilling off a peracetic acid concentrated agueous distillate from the reaction medium;
withdrawing reaction medium containing the acid catalyst from the reaction medium; and
obtaining a peracetic acid product by combining the distilled-off distillate with the withdrawn reaction medium and a neutralizing agent that at least partially neutralizes the acid catalyst.

2. A continuous process for the stable production of a stable peracetic acid product, comprising the steps of:
into a reaction medium comprising an acid catalyst, hydrogen peroxide, acetic acid, and peracetic acid, continuously feeding further hydrogen peroxide and further acetic acid to form further peracetic acid within the reaction medium;
continuously distilling off a peracetic acid concentrated aqueous distillate from the reaction medium;
withdrawing reaction medium containing the acid catalyst from the reaction medium; and
obtaining a peracetic acid product by combining the distilled-off distillate with the withdrawn reaction medium and a neutralizing agent that tends to neutralizes the acid catalyst.

3. A process for the stable production of a stable peracetic acid product, comprising the steps of:
preparing a reaction medium comprising an acid catalyst, hydrogen peroxide, acetic acid, and peracetic acid;
continuously feeding to the reaction medium further hydrogen peroxide and further acetic acid to form further peracetic acid within the reaction medium;
continuously distilling off a peracetic acid concentrated aqueous distillate from the reaction medium;
withdrawing reaction medium containing the acid catalyst from the reaction medium; and
obtaining a peracetic acid product by combining the distilled-off distillate with the withdrawn reaction medium and a neutralizing agent that at least partially neutralizes the acid catalyst.

4. The process according to claim 3, characterized in that the withdrawing of the reaction medium and combining the withdrawn reaction medium with the distillate and with the neutralizing agent are carried out continuously.

5. The process according to claim 4, characterized in that the reaction medium is removed at a desired ratio to the distillate and is combined with it and the neutralizing agent.

6. The process according to claim 3, characterized in that the reaction medium is removed batchwise, and the withdrawn reaction medium is combined with the distillate and the neutralizing agent.

7. The process according to claim 3, characterized in that the distillate, the reaction medium and the neutralizing agent are mixed together so that the weight ratio of the distillate to the reaction medium is within the range 1:50–500:1.

8. The process according to claim 3, characterized in that the distillate, the reaction medium and the neutralizing agent are mixed together so that the peracetic acid concentration in the mixture is 10–68% by weight.

9. The process according to claim 3, characterized in that the acid catalyst is an inorganic acid or a mixture thereof.

10. The process according to claim 3, characterized in that the distillate, the withdrawn reaction medium and the neutralizing agent are mixed together so that the weight ratio of the distillate to the reaction medium is within the range 1:1–100:1.

11. The process according to claim 3, characterized in that the distillate, the withdrawn reaction medium and the neutralizing agent are mixed together so that the weight ratio of the distillate to the reaction medium is within the range 10:1–30:1.

12. The process of claim 9, wherein the inorganic acid is one of phosphoric acid and sulfuric acid.

13. The process according to claim 9, characterized in that the concentration of sulfuric acid in the reaction medium is within the range 1–10% by weight.

14. The process according to claim 9, characterized in that the concentration of sulfuric acid in the reaction medium is within the range 1–4% by weight.

15. The process according to claim 13, characterized in that the concentration of sulfuric acid in the reaction medium is within the range 1–20% by weight.

16. The process according to claim 3, characterized in that the neutralizing agent is one of an inorganic base, a substance forming an inorganic base, and a mixture containing an inorganic base and a substance forming an inorganic base.

17. The process of claim 16, wherein the inorganic base is one of an alkali metal hydroxide, an alkaline earth metal hydroxide.

18. The process according to claim 3, characterized in that the neutralizing agent is sodium hydroxide and is mixed together with the distillate and the reaction medium as an aqueous solution having a concentration of 40–50% by weight.

19. The process according to claim 3, characterized in that the neutralizing agent is sodium hydroxide and is mixed together with the distillate and the reaction medium as an aqueous solution having a concentration of 20–60% by weight.

20. The process according to claim 3, characterized in that the neutralizing agent is combined with the distillate and the reaction medium in a substantially stoichiometric amount relative to the acid catalyst amount.

21. The process according to claim 3, characterized in that first the reaction medium and the neutralizing agent are mixed together to form a first mixture, the acid catalyst in which is substantially neutralized, and thereafter this first mixture is mixed together with the distillate.

22. The process according to claim 21, characterized in that the pH of the reaction medium before the mixing, to form the first mixture, is within the range 0.001–1.0.

23. The process according to claim 3, characterized in that the pH of the distillate before combining the distillate, the reaction medium and the neutralizing agent is within the range 1–3.

24. The process according to claim 3, characterized in that the distillate, the reaction medium and the neutralizing agent are combined so that the pH of the resulting mixture is within the range 1.0–3.0.

25. The process according to claim 3, characterized in that in connection with combining the distillate; the reaction medium, or the neutralizing agent, or the distillate, or the resulting mixture is cooled to a temperature within the range −10 to 0° C.

26. The process according to claim 21, characterized in that the pH of the reaction medium before the mixing, to form the first mixture, is within the range 0.02–0.2.

27. The process according to claim 3, characterized in that the distillate, the reaction medium and the neutralizing agent are combined so that the pH of the resulting mixture is within the range 1.3–1.5.

* * * * *